United States Patent [19]

Chance

[11] Patent Number: 5,553,614
[45] Date of Patent: Sep. 10, 1996

[54] EXAMINATION OF BIOLOGICAL TISSUE USING FREQUENCY DOMAIN SPECTROSCOPY

[75] Inventor: Britton Chance, Philadelphia, Pa.

[73] Assignee: Non-Invasive Technology, Inc., Philadelphia, Pa.

[21] Appl. No.: 76,370

[22] Filed: Jun. 14, 1993

Related U.S. Application Data

[63] Continuation of Ser. No. 645,590, Jan. 24, 1991, abandoned, which is a continuation-in-part of Ser. No. 287,847, Dec. 21, 1988, Pat. No. 5,119,815, and a continuation-in-part of Ser. No. 578,063, Sep. 5, 1990, Pat. No. 5,122,974, which is a continuation of Ser. No. 307,066, Feb. 6, 1989, Pat. No. 4,972,331.

[51] Int. Cl.$^6$ ........................................ A61B 5/00
[52] U.S. Cl. .......................... 128/633; 128/664
[58] Field of Search ................ 128/633, 63 X, 128/664, 665, 897, 898; 356/5

[56] References Cited

U.S. PATENT DOCUMENTS

| | | | |
|---|---|---|---|
| 3,360,987 | 1/1968 | Flower et al. | 356/5 |
| 3,365,717 | 1/1968 | Hölscher | 356/5 |
| 3,522,992 | 8/1970 | Jaffe | 356/5 |
| 4,458,694 | 7/1984 | Sollish et al. | 128/734 |
| 4,908,762 | 3/1990 | Suzuki et al. | 128/633 |

FOREIGN PATENT DOCUMENTS

| | | |
|---|---|---|
| WO89/00281 | 1/1989 | European Pat. Off. . |
| 156398 | 8/1982 | Germany . |
| 55-141656A | 5/1980 | Japan . |

OTHER PUBLICATIONS

Maarek et al., "Etude en simulation due comportement de la lumiere dans les tissues", Innovation Et Technologie En Biologie Et Medicine, vol. 7, No. 1, pp. 1986 294–307.
D. T. Delpy et al., "Estimation of optical pathlength through tissue from direct time of flight measurement", Phys. Med. Biol., vol. 33, No. 12, 1988 pp. 1433–1442, UK.
Chance et al., "Time resolved spectroscopy of hemoglobin and myoglobin in resting and ischemic muscle", Analytical Biochemistry, vol. 174, pp. 698–707, 1988.
Lackowicz, J. R., "Gigahertz Frequency–Domain Fluorometry: Resolution of Complex Intensity Decays, Picosecond Processes and Future Developments", Photon Migration In Tissues, Academic Press/NY, pp. 169–186 (1989).
Chance, B. et al., (1988) Proc. Natl. Acad. Sci. USA 85, pp. 4971–4975.
Chance, B. (Ed.), "Photon Migration in Muscles and Brain", in Photon Migration In Tissues, Academic Press/New York, pp. 121–135 (1989).
Chance, B. (1951) Rev. Sci. Instrum. 22, 619–627.
Chance, B. (1966) Biochemistry Of Copper, ed. Peisach, J. (Academic, New York), pp. 293–303.
Chance, B., Legallais, V. & Schoener, B. (1962) Nature (London) 195, 1073–1075.
Chance, B. (1954) Science 120, 767–775.
Chance, B. (1959) J. Biol. Chem. 234, 3036–3040.
Jobsis–VanderVlient, F. F. (1985) Adv. Exp. Med. Biol. 191, 833–842.
Jobsis, F. F. et al.,(1977) J. Appl. Physiol. 113, 858–872.

(List continued on next page.)

Primary Examiner—David M. Shay
Attorney, Agent, or Firm—Fish & Richardson P.C.

[57] ABSTRACT

The present invention discloses methods and apparatus for the quantitation and localization of tissue hypoxia by both time and frequency domain spectroscopy. The present invention provides several alternate embodiments of apparatus by which the saturation of a tissue region may be determined. In the time-resolved embodiment, a simplified system provides data which are directly proportional to the tissue saturation. In the phase modulating embodiments of the present invention, a first embodiment provides phase shift data which may be converted into saturation readings. A second embodiment, separates the real and imaginary portions of the signal and uses these data along with the data gathered from the DC portion of the signal to determine saturation. Methods of determining the hemoglobin concentration/oxygenation of a tissue region are also disclosed.

40 Claims, 2 Drawing Sheets

OTHER PUBLICATIONS

Rosenthal, M. et al., (1976) Brain Res. 108, 143–154.

vanderZee, P. et al. (1988) in Oxygen Transport To Tissue X, eds. Mochizuki, M. et al. (Plenum, New York) pp. 191–197.

Tamura, M. H. et al. (1987) in Chemoreceptors and Reflexes In Breathing, ed. Lahiri, S. (Oxford, New York) in press.

Duysens, L. (1964) Prog. Biophys. Mol. Biol. 14, 1–104.

Chance, B. (1952) Nature (London) 169, 215–230.

Blumberg, W. E. (1987) Biophys. J. 51, 288 (abstr.).

Bonner, R. F. et al., (1987) J. Opt. Soc. Am. Sec. A 4, 423–432.

Galeotti et al. (Eds.), Membrane in Cancer Cells, 551 N.Y. Acad. Sci. (1988) (preface).

EXAMINATION OF BIOLOGICAL TISSUE USING FREQUENCY DOMAIN SPECTROSCOPY

CROSS-REFERENCE TO RELATED APPLICATIONS

This is a continuation of application Ser. No. 07/645,590, filed Jan. 24, 1991, now abandoned, which in turn is a continuation-in-part of U.S. patent application Ser. No. 287,847, filed Dec. 21, 1988, which issued on Jun. 9, 1992 as U.S. Pat. No. 5,119,815 entitled "METHODS AND APPARATUS FOR DETERMINING THE CONCENTRATION OF A TISSUE PIGMENT OF KNOWN ABSORBANCE IN VIVO USING THE DECAY CHARACTERISTICS OF SCATTERED ELECTROMAGNETIC RADIATION"; and U.S. patent application Ser. No. 578, 063, filed Sep. 5, 1990 which issued on Jun. 16, 1992 as U.S. Pat. No. 5,122,974 entitled "PHASE MODULATED SPECTROSCOPY," which is a continuation of U.S. patent application No. 307,066, filed Feb. 6, 1989, now U.S. Pat. No. 4,972,331, issued Jul. 25, 1990, all of which are incorporated by reference as if set forth in their entireties herein.

BACKGROUND OF THE INVENTION

It is clear that a new field of study is emerging where previous limitations to the quantitation of the concentration of absorptive constituents in scattering media by continuous light (CW) approaches are overcome as information on both absorption and scattering parameters become available in homogeneous tissues, and localization possibilities ameliorate problems that arise with inhomogeneous tissues.

The incidence of hypoxia/ischemia and hemorrhage in pre-term neonates is well recognized and the need for early detection of these syndromes is apparent from the current studies using ultrasound and nuclear magnetic resonance. Other applications to neonatology, particularly brain hypoxia monitoring during cardiopulmonary bypass and other surgical procedures applied to the heart and even monitoring of brain hypoxia of the infant in the birth canal as affected by uterine contractions in prolonged deliveries signify other requirements for a reliable method of quantifying oxy-hemoglobin concentrations in vivo, in real time. In adults many similar applications emerge, ranging from brain hypoxia in surgical procedures of cardiopulmonary bypass or AICD testing (ventricular defibrillation), including monitoring of oxygenation of recently transplanted, liver, pancreas, etc., to the detection of altered blood flow or lack of blood flow in chronic brain disease such as Alzheimer's, Parkinson's, and multiple infarct dementia (MID). All of these applications dictate an apparatus which can be readily applied to the exposed tissue and collect sufficient data in times as short as the few seconds that may be required to make a significant reading; time is often of the essence in clinical diagnosis and decision making. Thus calibration procedures, etc., must either be made subsequent to the measurement or the system itself should be rapidly auto-calibrating during the study.

A completely different field of applications which also reflect the need for a reliable quantitative measure of oxy- or deoxy-hemoglobin is to the exercising human body either in a confined exercise test such as rowing ergometry, bicycle ergometry, or in strength testing devices, etc., where the motion of the muscle during contraction requires that the unit be firmly attached to the overlying skin. In this case, setup time prior to the exercise should be minimal and recordings of steady state deoxygenation of the muscle bed during exercise and the transient recovery following the exercise is required. Typical applications are to the testing of national rowers, to the triathlon (swimming, running and cycling), or equally important, the training and rehabilitation of muscle function following vascular surgery and the study of muscle atrophy due to extended bed rest, geriatric conditions, or space travel.

Thus, it is clear that a device which makes rapid and reproducible readings of hemoglobin deoxygenation and hemoglobin concentration is highly desirable. To be practical, however, such a device requires a high signal-to-noise ratio and a measurement algorithm that is highly robust, with some possibilities for localization.

The brain cortex and larger muscles of the leg (Vastus Lateralis, etc.) are relatively homogeneous whilst the inner layers of the brain and the muscles of the forearm are heterogeneous. Furthermore, diseased tissue, infarcted brain, the necrotic portion of tumors represent heterogeneities that are of especial interest in themselves and indeed if included in the measurement of neighboring tissues would give erroneous values of absorption and scattering. Thus, knowledge of photon propagation in tissues and judicious placement of input/output coupling is required for accurate spectroscopy, or acquisition of data sets appropriate for construction of an image.

In principle, time-resolved spectroscopy converts the measurement of concentration or intensities by transmitted or reflected light to the measurement of photon migration time delay or path length. This enables quantitation of concentration changes in highly scattering tissues which was not heretofore possible. The characteristics of such devices and its principles are described, for example, in the co-pending patent applications referenced above.

SUMMARY OF THE INVENTION

The present invention utilizes a novel combination of the technology of time and frequency domain spectroscopy to provide a system for imaging hemoglobin deoxygenation that fulfills and the medical/surgical requirements for patient monitoring and decision making discussed above.

Thus, in a preferred embodiment of the preferred invention a time sharing, time resolved spectroscopic apparatus for the quantitation of hemoglobin is disclosed which comprises a laser that transmits pulses of light alternately between two wavelengths via a fiber coupler into the subject. A detector receives migrating light and creates a signal which is amplified and then transmitted to a discriminator to provide TTL pulses. The apparatus uses a time to amplitude convertor to create amplitude signals which are then synchronized with the alternations of the frequency and transmitted to two dedicated multichannel analyzers which create an output signal. Finally, a signal processor converts the output signals into a ratio of the terminal slopes of the intensity of the pulses over time and this ratio is directly proportional to the hemoglobin saturation in the tissue of the subject.

In another preferred embodiment of the present invention frequency domain spectroscopic apparatus are provided which can provide quantitation data for the hemoglobin concentration in the tissue of the subject. In this embodiment, a laser and detector are again used to alternately pulse two wavelengths of electromagnetic radiation into a subject where the received signals are amplified. A phase detector is used to determine the phase shift between the transmitted pulse and the output signal detected. An electronic switch means which is synchronized with the alternations of the pulses separates the alternate wavelengths and transmits them into a signal processor which create output signals indicative of the sum, the difference and a ratio of the phase signals. These data can be converted into a value of hemoglobin saturation.

In still another embodiment of the present invention, frequency domain spectroscopic apparatus for the quantitation of hemoglobin concentration and in tissue region are disclosed which again use an alternately pulsed laser and detector to transmit light through the tissue of a subject. The received signal is again amplified and is then transmitted to two double balanced mixers as well as being transmitted to a phase detector. The double balanced mixers also receive a reference phase shift signal which has been set to zero and fed through a 90° splitter. The output of each of the double balanced mixers is transmitted to sychronizing circuits which respectively separate the real and imaginary portions of the signal for each of the two wavelengths. The phase detector signal is also transmitted to a synchronizing circuit which separates the signal into DC portions corresponding to each of the respective wavelengths. Finally, signal processing means are provided which obtain the process signals indicative of the phase shift and amplitude of the detected signal. These processed signals can then be converted into signals indicative of the modulation index of the tissue at each of the wavelengths.

Methods of determining the concentration of hemoglobin within a tissue region are also disclosed.

DETAILED DESCRIPTION OF THE PREFERRED EMBODIMENTS

The availability of pulsed laser diode light sources and the knowledge that large tissue volumes such as the adult head exhibit photon migration lasting 5– nsec open the possibility that "slow" detection systems such as the squirrel cage photomultipliers, become extremely attractive especially since the latter can be obtained with extended red response which is most suitable for tissue measurements. Silicon diodes, especially of the avalanche type, are of adequate speed but have such a small sensitive area that the need for multiple detectors or appropriate light gathering systems has currently limited their application to large tissue volumes such as adult brain, etc. These components, together with simplified photon counting systems, make time-resolved systems practical for portable use. In fact, currently available tissue spectrophotometers can readily be converted to time domain spectroscopy by the use of pulsed laser diodes and improved photon counting technology.

Figure 1:
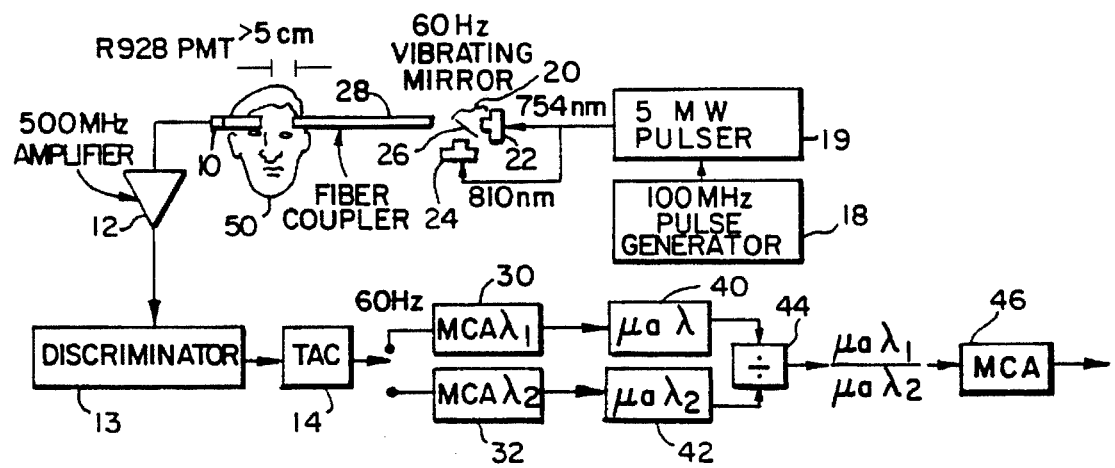
FIG. 1 is a schematic representation of a time-resolved spectrophotometer.

The configuration of a simplified and portable time domain system for tissue studies is shown in the block diagram of FIG. 1, where a "squirrel cage" photomultiplier detector 10 and a laser diode light source 20 are employed. This system serves the need for a more sophisticated and compact time correlated single photon counting (TCSPC) system. As shown in FIG. 1, in a preferred embodiment of this system, Hamamatsu PLP-10 pulsed laser diodes 22, 24 are operated at 10 MHz repetition frequency and at wavelengths of 754 nm and 810 nm. The laser diodes 22, 24 are driven by a 100 MHz pulse generator 18 connected to a 5 mW pulser 19 that drives both diodes. In this embodiment, a fiber coupler 28 conducts pulses of light into the subject 50. The light from the two laser diodes 22, 24 is time shared electromechanically by a 60 Hz vibrating mirror 26 so that they alternately illuminate the fiber coupler 28. The transmitted photons migrate through the subject 50 to the detector 10. Using this configuration the extended red sensitive squirrel cage photomultiplier 10 can be employed for studies of human brain at input/output fiber separations of greater than 5 cm as shown. The instrument function shows a 1 nanosecond FWHM response for this detector. The R928 photomultiplier tube 10 for non-imaging spectroscopy can be coupled directly to the forehead to provide a detector area of 200 square millimeters. In an alternate embodiment, a fiber optics coupling (not shown) with an area of 20 square millimeters can be employed—with an obvious decrease in the signal to noise ratio, but providing increased spatial resolution.

The output of the photomultiplier tube 10 is directly connected to a wide band amplifier 12 with appropriate roll-off to give good pulse shape and optimal signal to noise ratio. A high/low level discriminator 13 receives an output signal from the amplifier 12 and gives TTL pulses to a time to amplitude convertor (TAC) 14. Following the time to amplitude conversion, the counts corresponding to the two wavelengths are separately summed in two multichannel analyzers (MCA) 30, 32. The outputs of the multichannel analyzers 30, 32 can be used to calculate signals 40, 41 indicative of the terminal slopes: $\mu_a\lambda_1$ and $\mu_a\lambda_2$. These are divided in a division step 44, since their ratio is simply converted into the saturation of hemoglobin. The pulses are then preferably accumulated in a 1,000 bin multichannel analyzer 46 over a sufficient interval so that approximately $10^5$ counts are collected at the maximum in order that the logarithmic slope be followed down for three or four decades of intensity. The stored information on the slopes of the two wavelengths is then processed by creating a set of ratios and a logarithm is employed in order to conveniently calculate saturation using the formula:

$$Y(\times 100\%) = \frac{38 - 17 \dfrac{\mu_a^{754}}{\mu_a^{816}}}{25 + 9 \dfrac{\mu_a^{754}}{\mu_a^{816}}} \tag{1}$$

This embodiment of the present invention also permits the scattering factor to be calculated, particularly when fits to the data have been obtained by a diffusion equation. If input/output distances smaller than 5 centimeters are desired, then the input function can be convoluted with the solution to the diffusion equation, which then is fitted to the experimental curve. An instrument made in accordance with this embodiment of the present invention has attractive possibilities of portability, and the readout algorithm for saturation is readily computed from the extinction coefficients according to the equation set forth above. This embodiment, with the aid of an extended red sensitive photomultiplier, can accumulate satisfactory data in several minutes, but does not approach the speed of a phase modulated system.

As understood by those of ordinary skill, the data collected and signals obtained by the embodiment described above can be further analyzed. The Fourier transform of the domain kinetics give phase and amplitude compounds that contain all the time domain information, and adequate information for concentration determinations in the dual wavelength mode, which is available for both.

The present invention also provides novel frequency domain systems which determine hemoglobin concentrations. Phase modulation spectroscopy has been shown to be well adapted to the measurement of photon migration parameters in the human brain and in model systems. Multi-frequency systems are available and have proved invaluable in this research for studies of the frequency/phase diagrams and for phase modulation imaging of tissues. It has been shown to be desirable to design simple phase modulation systems for clinical applications. Such designs however, require significant precision, since, as discussed above, it is convenient to employ frequencies within the range of the squirrel cage photomultiplier in systems where the limitations of the photodetector frequencies to 200 MHz, phase shifts of the order a few degrees, and path length changes of a few centimeters are characteristic. Thus, oscillator precision, leakage of excitation signal into the receiving channel, drift of the phase detector, and cross-talk between the channels representing the two wavelengths employed have all been problems which can be readily solved by the present invention, as described below.

Figure 2:
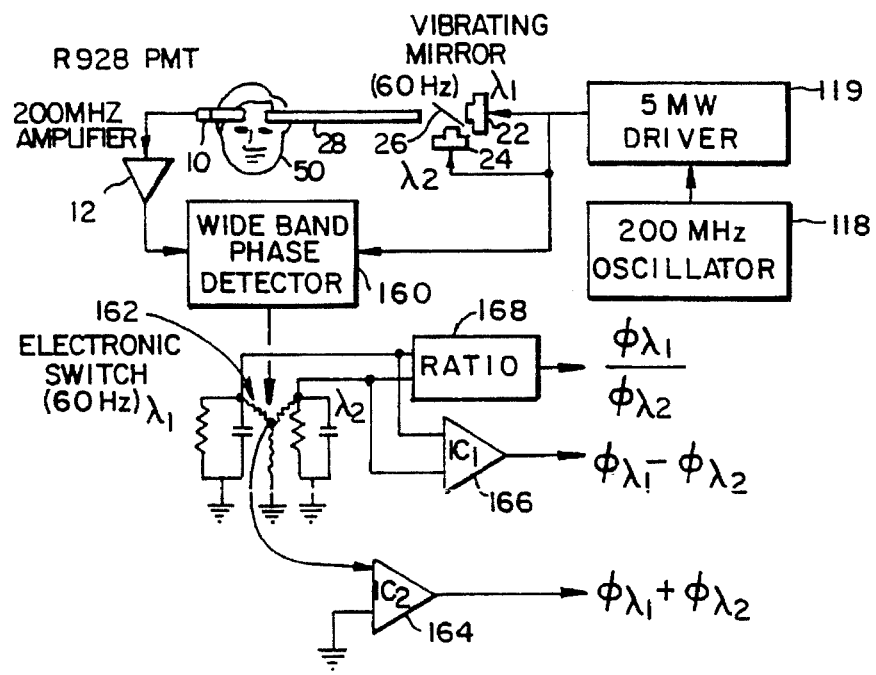
FIG. 2 is a schematic representation of a frequency domain spectrophotometer.

A simplified system for frequency domain studies is illustrated in FIG. 2. Rather than using a pulse generator, this embodiment utilizes a 200 MHz precision oscillator 118 which drives two laser diodes 22, 24, again at 760 and 816 nm, the outputs of which are time shared into a fiber optic coupling 28 to the head 50 as illustrated. At this frequency, the input/output separations can be varied from 10–5 cm as desired and either the total output from the sensitive area of photocathode (200 square millimeters) can be used or that of a fiber optics coupling from a smaller area, as in the case of the time domain system described above with reference to FIG. 1. Whilst usually an oscillator displaced some 20 KHz from the 200 MHz oscillator is used to provide a low frequency heterodyne signals, as described in my co-pending patent application referenced above, the availability of wide band phase detectors makes it attractive to couple the 200 MHz signal directly into such a wide band phase detector chip 160 as indicated in FIG. 2, with time shared outputs corresponding to the two light intensities. In order to demodulate these outputs, an electronic switch 162 synchronized with the vibrating mirror 26 is employed so that the phase delay at the two wavelengths is available as the ratio the difference, or the sum for appropriate calculations of the saturation according to the equality:

$$\frac{\theta^{\lambda_1} - \theta_0^{\lambda_1}}{\theta^{\lambda_2} - \theta_0^{\lambda_2}} = \frac{\mu_a^{\lambda_1}}{\mu_a^{\lambda_2}}$$

Research has shown that $\theta_0$ can be determined from the hemoglobin free scattering properties of the brain tissue. Thus, the three outputs of the electronic switch 162 may be fed to processing circuits 164, 166 which create a sum and difference respectively. The phase outputs are also combined in a circuit 168 to create a ratio. The selection and construction of the logic devices, e.g., the integrated circuits disclosed herein and the like, is well known to those of ordinary skill.

The term $\theta_0$ limits the applications of single-frequency modulated spectroscopy to tissues where $(1-g)\mu_s$ can be estimated a priori and is not expected to change such as might happen during disease, treatments such as radiotherapy, or even transfer from animal models to tissue. There are, however, two approaches to utilizing the approximation which circumvent this problem: (i) to employ an additional third wavelength; and (ii) to employ dual-wavelength, dual-frequency phase-modulation techniques. In the first approach, the ratio of absorption coefficients for two sets of wavelengths are used to solve for $\theta_0$ such that both ratios of absorption coefficients predict identical hemoglobin saturations, Y. In the second approach, measurement of phase shifts at dual-wavelength and dual-frequencies, where $2\pi f_1$, $2\pi f_2 \gg \mu_a^{\lambda_1} c, \mu_a^{\lambda_2} c$, can give information of hemoglobin saturation from transmittance geometries. Thus, a preferred embodiment of the invention disclosed herein employs phase modulated spectrophotometers capable of time-shared, dual-wavelength, dual-frequency measurements.

Referring still to FIG. 2, a block diagram of a time shared phase modulation system in which two wavelengths are available is shown. This system provides appropriate sums and differences and ratios of the signal utilizing a vibrating mirror 26 for time sharing of the two laser wavelengths. This simplifies the oscillator system, as only two are required and only one phase detector. The difference or ratio circuits afford cancellation of common mode errors to a great extent affording high performance with a simple system.

Figure 3:
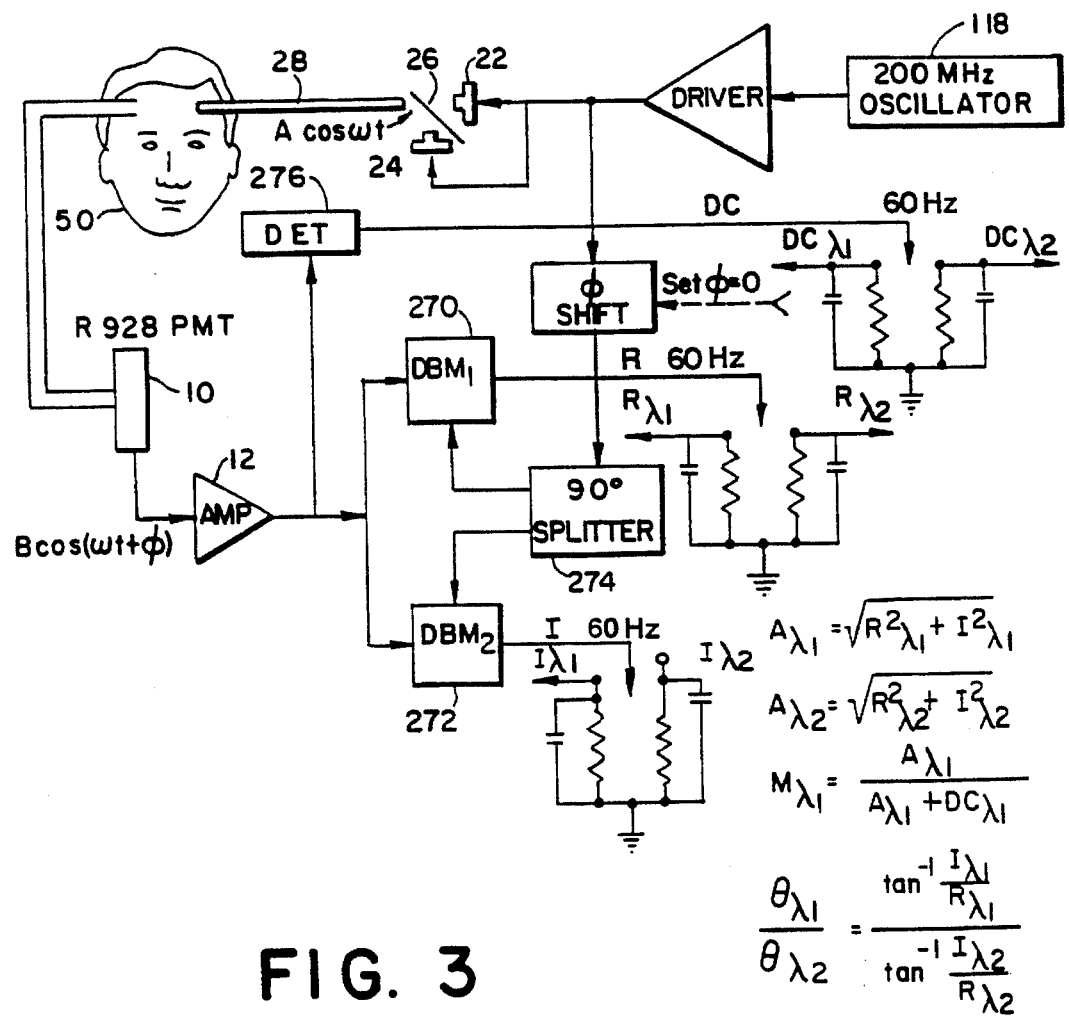
FIG. 3 is a schematic representation of a time-shared/phase modulated spectrophotometer.

An alternate way of handling the data output from the system of FIG. 2 is illustrated in FIG. 3 where the detector output is put through two wide band double balance mixers (DBM) 270, 272 which are fed through a 90° phase splitter 274 so that real (R) and imaginary (I) portions of the signal are obtained. The double balance mixers 270, 272 preferably operate at the modulation frequency. The phase $\phi$ is the angle whose tangent is the imaginary over real part, whilst the amplitude is the square root of the sum of the squares of these values, providing the phase shift has been taken out as the residual phase shift $\phi$ set to zero as indicated. Thus this embodiment of the present invention provides the modulation index, which is the quotient of the amplitude over the amplitude plus the DC component obtained from a narrow band detector 276 as shown in FIG. 3. A synchronous detector de-codes the phase shifts for the phase and amplitude values for the two wavelengths so that the ratio of the phase shifts may be obtained as indicated in the previous diagrams. In order to obtain the proper functions, the ratio of the $\theta$'s and the correct value of amplitude, a ratio circuit divides the I and R terms and the angle is computed; in this case, the small angle approximation is valid and the ratio circuit computes $\theta \lambda_1/\theta \lambda_2$ as required for the equation set forth with reference to FIG. 2 above. In the case of the amplitude function, the square root of the sum of the squares are computed to obtain the amplitude and the summing and dividing circuits calculate the modulation index at the two wavelengths.

Some of the components of the embodiments of the present invention described above with reference to FIGS. 1–3 are of especial interest, e.g., the requirements for the laser diodes 22, 24 are that the low power, 5 mW laser diodes be modulated near 100% to give signals appropriate for tissue studies. The phase modulated information is obtained from a significant volume of tissue surface. A second and important feature is the stability of crystal oscillators requiring appropriate electronic construction and tuning parameters. The performance values are drift of 0.2 mm/hr and phase noise<0.9 mm in a 0.1 Hz band width. Signal changes are usually 1–2 cm in a 23 cm path length. Wavelengths of the laser diodes 22, 24 are preferably on opposite sides of the cross over or isosbestic point between the oxy- and deoxy-hemoglobin absorption spectrum (about 800 nm) are used so that the difference of the signals represents a change on deoxygenation whilst the sum represents the total amount of hemoglobin present of the desirable quantities mentioned above.

Data display is of considerable importance to the functioning of the apparatus of the present invention, as is computer coupling. A running time LCD display is preferably used for monitoring in order to ensure that signals are within the linear range of the phase detector, together with a LED indicator, indicating that the signal amplitude does not reach predetermined limits. In addition, the computer coupling to obtain manipulated data from wave saturation may be obtained as necessary.

Various formulations by which the path length changes measured in time and frequency domain studies can be simply converted into concentration changes using appropriate wavelengths and appropriate extinction coefficients have been presented. Whilst the biochemist requires the determination of a tissue concentration, the physiologist is content with the saturation percentage change of one form with respect to another, usually the oxy with respect to the total (oxy+deoxy) in the case of hemoglobin. These algorithms generally involve the ratio of the path lengths determined at a pair of wavelengths as indicated in the discussion above. However, those of ordinary skill will appreciate that other absorbers can also be studied. For example, injected indocyanine-green (a flow indicator), or naturally occurring absorbers such as fat, protein, water may be studied by photon migration techniques such as those utilized by the present invention.

The coupling of the system to the subject 50 is of importance and whilst this can be done satisfactorily with plastic light guides 28, usually of an area for receiving of 2 square centimeters, direct contact of a large area detector with the subject's skin is desirable if the input/output separation exceeds 5–10 cm, as is the case in an adult. Similarly, whilst spectroscopy requires signal acquisition from large surface areas, imaging upon this area sets limitations to about 1 cm signals from a large number of points around the circumference of the human head are desirable for planar imaging of brain bleeding.

The performance of the phase modulation systems disclosed above have been experimentally determined, together with quantification of the drift, noise and other parameters. For example, the performance of the laser diode light source and squirrel cage detector as applied to a model system and a human head have been noted. While animal models provide excellent systems for quantifying the performance of both time resolved and phase modulated systems the exercising human muscle is optimal for the validation of the functionality of the system, particularly in terms of the signal-to-noise ratio in an actual in vivo system.

This application has presented three systems for time and frequency domain spectroscopy, each one capable of measurement of hemoglobin saturation and blood volume. The most comprehensive measurement is given by that of FIG. 1 since the entire time profile of photon decay is measured and if measured at longer times, is independent of $\mu_s$. Perhaps the most important feature of the instrumentation is that the variation of time delay with photomultiplier voltage is not as a primary factor, as long as the logarithmic slopes, $\mu_a$ values, are read out at longer times, i.e., 5–10 ns. Thus, this system is optimal for the adult human head where long path lengths and large separations of input/output are available.

Systems of FIGS. 2 and 3 are suitable for shorter path lengths as are observed in skeletal muscle or neonates. The system of FIG. 3 gives comprehensive information which if available at a number of frequencies and appropriately Fourier transformed would have the same information content as the pulse time method. When restricted to particular carrier frequencies, the method nevertheless retains its quantitation of hemoglobin saturation through the ratio of the θ values and affords in addition the modulation index. Thus, this unit would have unique properties for imaging, brain bleeding, or other localized depots of hemoglobin. The system is in effect to be significantly faster than that of FIG. 1 by a factor of 10 or perhaps more.

The system of FIG. 2 is the simplest system requiring only a small number of chips to afford the ratio of phase shifts necessary for the calculation of saturation. This system is also quite fast, time constants of 5 sec probably being appropriate for brain recording.

The system of FIG. 1 is not expected to need calibration except for its own instrument function which is expected to be constant for a given dyode voltage on the photomultiplier and to vary insignificantly with small changes thereof. The system of FIGS. 2 and 3 will require calibration for the values of θ although it should be noted that the ratio of these values is acceptable and thus the calibration errors will only be of secondary importance. Obviously, the rapid development of available electronic circuitry, particularly in the region of 100–500 MHz will result in further simplifications of the apparatus displayed here. At the present time, the use of time shared laser diode wavelengths and the calculation from the ratio of phase shifts of the saturation value allows much greater freedom from drift and background signals than for a single wavelength system. Obviously, as many wavelengths as desired can be obtained by time sharing.

The goal of the certain preferred embodiments of the present invention therefore, is to indicate what is needed in order to acquire appropriate data for the study of brain tissue hypoxia. The first requirement is obviously of a system of adequate accuracy and reproducibility; the requirements being approximately 1 mm in distance or 0.001 in logarithmic slope (i.e., a corresponding value in mm). Absolute stability is less stringent, but nevertheless, the measurement requires the difference or ratio of slopes for the determination of saturation and for the absolute concentration. The second major requirement is to select wavelengths at which an adequate signal is generated, i.e., one in which the change of hemoglobin saturation or concentration gives a significant change of path length. Also, ready calibration is necessary. For animal models, 100% change can readily be obtained by ischemia and hypoxia, however, for the study of human subjects, the range from 40% to 80% saturation is the maximum that could be expected under conditions of patient stability. The "normal" variations may be ⅕th of this for 8 to 10%. Thus, the "oxygen saturation" of the brain study requires a very high level of stability and reproducibility and stable calibration.

Certain embodiments of the present invention can determine hemoglobin saturation from measurements of phase-shift and modulation at varying modulation frequency. It has been found that $\mu_a^\lambda$ may be identified from reflectance and transmittance measurements of phase-shift, θ, and demodulation of the detected signal, M, as a function of modulation frequency, f. Theoretical considerations show that the critical phase and modulation frequencies, $f_o^\theta$ and $f_o^M$, at which the magnitude of the θ and M versus f slopes reach minima, are functions $\mu_a$ alone, regardless of $(1-g)\mu_s$ or of the source and detector configuration. From the ratio of critical frequencies identified from phase-shift and modulation spectra, the ratio of absorption coefficients can be found:

$$\frac{f_o^{\mu\lambda_1}}{f_o^{\mu\lambda_2}} = \frac{f^{0_1\lambda_1}}{f^{0_1\lambda_2}} = \frac{\mu_a^{\lambda_1}}{\mu_a^{\lambda_2}}$$

Sensitivity of this technique increases with enhanced tissue scattering and minimal absorption as is the characteristic of the brain. Thus, $f_o^0$ and $f_o^M$, might be identified from experimental spectra of media with physiological scattering properties to determine whether differential frequency-resolved spectroscopy may be used to accurately quantitate tissue oxygenation.

Although certain embodiments of the present invention have been set forth above with particularity, the invention is by no means limited to these embodiments. Upon review of the instant specification those of ordinary skill will realize numerous variations or adaptations to the methods and apparatus disclosed. For example, certain modifications can be made to the circuits disclosed or their application which still lie within the spirit of the invention disclosed. Accordingly, reference should be made to the appended claims in order to determine the scope of the present invention.

What is claimed is:

1. A phase modulation spectroscopic system for examination of biological tissue of a subject, the scattering and absorptive properties of the examined tissue being determined by photons migrating between an optical input port and an optical detection port of said system, said system comprising:

an optical input port located at a first location to introduce light to biological tissue;

an optical detection port located at a second location at the tissue spaced apart from said input port;

an oscillator, connected to a driver, that generates a carrier waveform of a selected frequency compatible with time delay of photon migration from said input port to said detection port;

a light source, connected to said input port and connected to receive from said oscillator or said driver said carrier waveform, said light source generates over time optical radiation of a selected wavelength that is intensity modulated at said frequency and introduces said optical radiation to the tissue at said input port;

an optical detector, connected to said detection port, said detector detects over time scattered photons of the introduced radiation that has migrated in said tissue of the subject between said input and detection ports and produces a detector signal;

a phase splitter connected to receive said carrier waveform from said oscillator or said driver and produce first and second reference phase signals of predefined substantially different phases;

first and second double balanced mixers connected to receive over time from said phase splitter said first and second reference phase signals, respectively, and connected to receive from said detector said detector signal and produce therefrom a real output signal and an imaginary output signal, respectively; and a signal processor connected to said double balanced mixers, said processor receives said real output signal and said imaginary output signal and determines therefrom a selected characteristic related to scattering or absorptive properties of said biological tissue.

2. The system of claim 1 wherein said selected characteristic is a phase shift ($\Theta_\lambda$) between the radiation introduced at said input port and the radiation detected at said detection port.

3. The system of claim 1 wherein said wavelength is a visible or infrared wavelength.

4. The system of claim 1 wherein said phases of said first and second reference phase signals have a 90 degree difference.

5. The system of claim 1 wherein said selected characteristic is an average migration pathlength of photons scattered in the examined tissue between said optical input port and said optical detection port.

6. The system of claim 5 wherein said signal processor further employs said pathlength in quantifying hemoglobin saturation (Y) of the examined tissue.

7. The system of claim 1 wherein said selected characteristic is a signal amplitude ($A_\lambda$) determined as a square root of a sum of squares of said real output signal and said imaginary output signal.

8. The system of claim 7 further comprising:

a narrow band detector connected to and receiving from said optical detector said detector signal to produce a DC output signal therefrom; and said signal processor further determines a modulation index ($M_\lambda$) as a ratio of values of said signal amplitude and said signal amplitude plus said DC output signal.

9. The system of claim 1 further comprising:

a second light source connected to said input port and connected to receive from said oscillator or said driver said carrier waveform, said second light source generates electromagnetic radiation of a second selected wavelength that is intensity modulated at said frequency;

said optical detector further detects, at said detection port, the radiation of said second wavelength that has migrated in said tissue between said input and detection ports; and a first and a second electronic switch, connected to receive, said real output signal and said imaginary output signal from said first and said second double balanced mixers, respectively, said first and a second switches separating for each said wavelength said real and imaginary signals, respectively.

10. The system of claim 9 further comprising:

a third light source, connected to said input port and connected to receive from said oscillator or said driver said carrier waveform, said third light source generates electromagnetic radiation of a third selected wavelength that is intensity modulated at said frequency;

said optical detector further detects, at said detection port, the radiation of said third wavelength that has migrated in said tissue between said input and detection ports; and said first and said second electronic switches connected to receive said real output signal and said imaginary output signal from said first and said second double balanced mixers, respectively, said first electronic switch and said second electronic switch separating said real and imaginary signals, respectively, at each of the three wavelengths.

11. The system of claim 9 or 10 wherein said selected characteristic is a signal amplitude ($A_\lambda$), at each said wavelength, determined as a square root of a sum of squares of said real output signal and said imaginary output signal at said wavelength.

12. The system of claim 11 further comprising:

a narrow band detector connected to and receiving from said optical detector said detector signal to produce a DC output signal;

a third electronic switch connected to said narrow band detector to receive said DC output signals and isolate said DC signals at each wavelength, said first, second and third electronic switches operating synchronized together; and said signal processor further determines, at each wavelength, a modulation index ($M_\lambda$) as a ratio of values of said signal amplitude and said signal amplitude plus said DC output signal.

13. The system of claim 9 or 10 wherein said selected characteristic is a phase shift ($\Theta_\lambda$) between the radiation introduced at said input port and the radiation detected at said detection port, determined at each wavelength.

14. The system of claim 9 or 10 wherein said selected characteristic is an average pathlength of photon scattered in the examined tissue between said input and detection ports of radiation at said selected wavelength.

15. The system of claim 9 or 10 wherein said wavelengths are visible or infrared wavelengths.

16. The system of claim 13 wherein said signal processor further determines a ratio of said phase shifts at two selected wavelengths.

17. The system of claim 16 wherein said signal processor determines hemoglobin saturation (Y) based on said ratio of phase shifts.

18. The system of claim 1, 9 or 10 wherein said oscillator operates at different selected frequencies of said carrier waveform.

19. A spectroscopic method of examination of biological tissue of a subject, the subject lying between an optical input port and an optical detection port of a phase modulation spectroscopic system that utilizes photons migrating between said ports over optical paths dependent on scattering and absorptive properties of the examined tissue, the method comprising the steps of:

generating a carrier waveform of a selected frequency compatible with time delay of photons migration from said input port to said detection port, introducing into the tissue of a subject, at said input port, electromagnetic radiation of a selected wavelength, said radiation having been intensity modulated at said carrier waveform;

detecting over time, at said detection port, the radiation that has migrated over said paths in said tissue between said input and detection ports;

creating a first and a second reference phase signals of predefined substantially different phases comparing over time said detected radiation with said first and said second reference signals and determining therefrom a real output signal and an imaginary output signal, respectively; and examining, on the bases of said real output signal and said imaginary output signal, the tissue by calculating a selected characteristic related to the scattering or absorptive properties of the tissue.

20. The method of claim 19 wherein said calculating said selected characteristic includes calculating a phase shift between the radiation introduced at said input port and the radiation detected at said detection port.

21. The method of claim 19 wherein said creating step includes creating said first and second reference phase signals which differ by 90 degrees.

22. The method of claim 19 wherein said calculating said selected characteristic includes calculating an average migration pathlength of photons scattered in the examined tissue between said optical input port and said optical detection port.

23. The method of claim 22 further including employing said pathlength in quantifying hemoglobin saturation (Y) of the examined tissue.

24. The method of claim 19 wherein said calculating said selected characteristic includes calculating a signal amplitude ($A_\lambda$) determined as a square root of a sum of the squares of said real output signal and said imaginary output signal.

25. The method of claim 24 further comprising the steps of:

determining DC signal from said detected radiation; and calculating a modulation index ($M_\lambda$) based on said DC signal and said signal amplitude.

26. The method of claim 19 further comprising the steps of:

introducing into the tissue at said input port electromagnetic radiation of a second selected wavelength modulated by said carrier waveform;

detecting, at said detection port, the radiation of said second wavelength that has migrated over said paths in said tissue between said input and detection ports;

comparing said detected radiation of said second wavelength with said first and said second reference signals and determining therefrom a real output signal for said second wavelength and an imaginary output signal for said second wavelength, respectively; and examining, on the bases of said real output signal and said imaginary output signal, at each of said selected wavelengths, the tissue by calculating a selected characteristic related to the scattering or absorptive properties of the tissue.

27. The method of claim 26 further comprising the steps of:

introducing into the tissue at said input port electromagnetic radiation of a third selected wavelength modulated by said carrier waveform;

detecting, at said detection port, the radiation of said third wavelength that has migrated over said paths in said tissue between said input and detection ports;

comparing said detected radiation of said third wavelength with said first and said second reference signals and determining therefrom a real output signal for said third wavelength and an imaginary output signal for said third wavelength, respectively.

28. The method of claim 26 or 27 wherein said calculating said selected characteristic includes calculating a phase shift, determined at each wavelength, between the radiation introduced at said input port and the radiation detected at said detection port.

29. The method of claim 28 further comprising the step of determining a ratio of absorption coefficients of said radiation at each said wavelengths based on a ratio of the corresponding phase shifts.

30. The method of claim 29 further comprising the step of determining hemoglobin saturation (Y) of said examined tissue based on said ratio of absorption coefficients.

31. The method of claim 26 or 27 wherein said calculating said selected characteristic including calculating a signal amplitude ($A_\lambda$) for each of said wavelengths determined as a square root of a sum of the squares of said real output signal and said imaginary output signal for each of said wavelengths.

32. The method of claim 31 further comprising the steps of:

determining at each wavelength DC signal from said detected radiation; and calculating at each wavelength a modulation index ($M_\lambda$) based on said DC signal and said signal amplitude.

33. The method of claim 19, 26 or 27 further comprising the step of amplifying said detected radiation before said comparing step.

34. The method of claim 19, 26 or 27 wherein said steps are performed at a second selected frequency and further comprising the step of:

examining said tissue by employing selected characteristics determined at least two wavelengths and at least two frequencies.

35. The method of claim 19, 26 or 27 wherein said selected wavelength is in the range of visible and infra-red wavelengths.

36. The method of claim 26 or 27 wherein two of said selected wavelengths are on opposite sides of the isobestic point between the oxy-hemoglobin and deoxy-hemoglobin absorption and said processor calculates a sum or a difference of the detected signals.

37. The method of claim 19, 26 or 27 wherein said introducing step includes utilizing said selected wavelength which affected by to an injected absorber.

38. The method of claim 19, 26 or 27 wherein said introducing step includes utilizing said selected wavelength affected by indocyanine-green.

39. The method of claim 19, 26 or 27 wherein said introducing step includes utilizing said selected wavelength which affected by a naturally occurring absorber.

40. The method of claim 39 wherein said naturally occurring absorber is one of the following: fat, water and a protein.

* * * * *

UNITED STATES PATENT AND TRADEMARK OFFICE
CERTIFICATE OF CORRECTION

PATENT NO. : 5,553,614

DATED : September 10, 1996

INVENTOR(S) : Britton Chance

It is certified that error appears in the above-identified patent and that said Letters Patent is hereby corrected as shown below:

On title page,
    item No. [56], line 3, under "Other Publications", after "1", please delete "pp.".

item No. [56], line 3, under "Other Publications", after "1986", please insert --pp.--.

Col. 3, line 46, after "5-", please insert --10--.

Claim 21, Col. 11, line 62, after "differ", please insert --in phase--.

Claim 34, Col. 13, line 10, after "at", please insert --at--.

Claim 34, Col. 13, line 10, after "and at", please insert --at--.

Claim 37, Col. 14, line 5, after "which", please insert --is--.

Claim 37, Col. 14, line 5, please delete "to".

Claim 38, Col. 14, line 8, before "affected", please insert --which is--.

UNITED STATES PATENT AND TRADEMARK OFFICE
CERTIFICATE OF CORRECTION

PATENT NO. : 5,553,614
DATED : September 10, 1996
INVENTOR(S) : Britton Chance

It is certified that error appears in the above-indentified patent and that said Letters Patent is hereby corrected as shown below:

Claim 39, Col. 14, line 12, after "which", please insert --is--.

Signed and Sealed this

Second Day of December, 1997

Attest:

Attesting Officer

BRUCE LEHMAN

Commissioner of Patents and Trademarks